United States Patent [19]

Tam

[11] Patent Number: 5,144,006
[45] Date of Patent: Sep. 1, 1992

[54] OXIDATIVE FOLDING OF PEPTIDE AND PROTEIN SUBSTRATES USING HYDROCARBON SULFOXIDES

[75] Inventor: James P. Tam, New York, N.Y.

[73] Assignee: The Rockefeller University, New York, N.Y.

[21] Appl. No.: 714,659

[22] Filed: Jun. 13, 1991

[51] Int. Cl.$^5$ ............ C07K 17/00; C07K 15/00; C07K 3/02
[52] U.S. Cl. ............ 530/345; 530/344; 530/354; 530/356; 530/357; 530/360; 530/397; 530/399
[58] Field of Search ............ 530/54, 56, 57, 360, 530/399, 397, 344, 345

[56] References Cited

U.S. PATENT DOCUMENTS

| | | | |
|---|---|---|---|
| 4,512,922 | 4/1985 | Jones et al. | 530/399 |
| 4,652,630 | 3/1987 | Bentle et al. | 530/344 |
| 4,694,073 | 9/1987 | Bentle et al. | 530/399 |
| 4,731,440 | 3/1988 | Bentle et al. | 530/399 |
| 4,745,178 | 5/1988 | DiMardi et al. | 530/345 |

Primary Examiner—Howard E. Schain
Attorney, Agent, or Firm—Wyatt, Gerber, Burke & Badie

[57] ABSTRACT

Method for oxidative folding of peptide and protein substrates to form disulfide bonds using dimethyl sulfoxide and other equivalent sulfoxides as mild oxidizing agents.

7 Claims, 7 Drawing Sheets

| Analog | Sequence (+100) |
|---|---|
| | 0 1 2 3 4 5 6 7 8 9 10 11 12 13 14 15 |
| FGF(100-115) | S N N Y N T Y R S R K Y T S W Y |
| TY-11(6) | ─────────────C───── |
| CY-11(7) | ──────────────C──── |
| CY-11(8) | ───────────────C─── |
| CY-11(9) | ────────────────C── |
| CY-12(9) | ────C──────────── |
| CY-12(10) | ─────C─────────── |
| CY-12(11) | ──────C────────── |
| NC-12(10) | ───────C───────── |
| SY-16(10) | ─────────C─────── |

FIG. 1

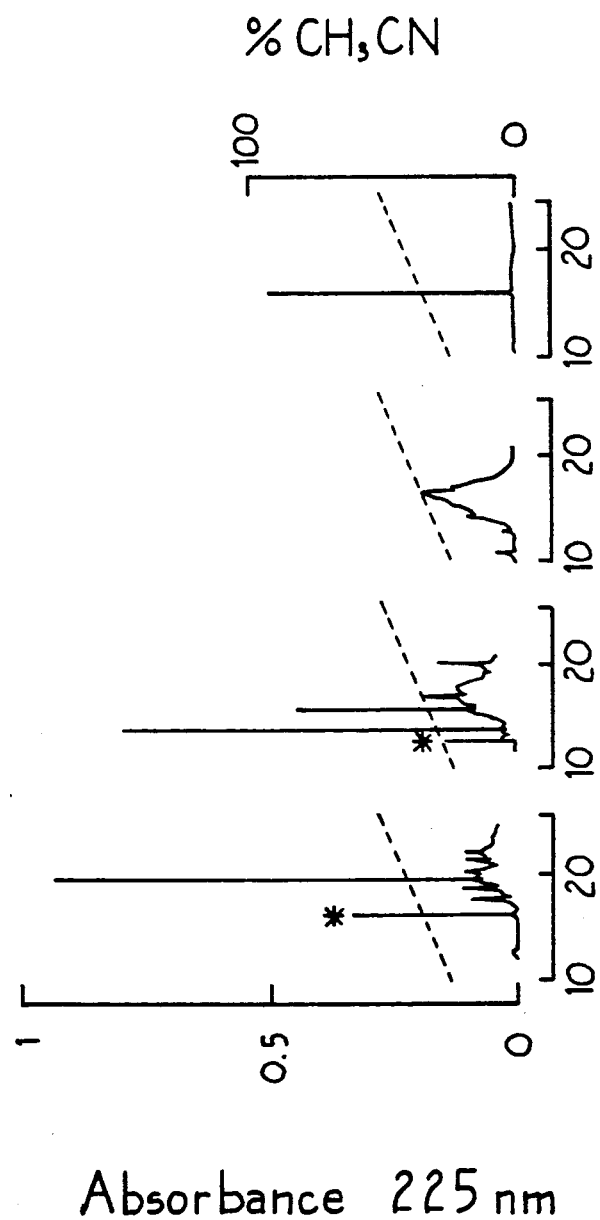

OXIDATIVE FOLDING OF PEPTIDE AND PROTEIN SUBSTRATES USING HYDROCARBON SULFOXIDES

BACKGROUND OF THE INVENTION

Disulfides in proteins play an important role in the maintenance of biological activity and conformational stability. It is possible to produce peptides and proteins having the correct sequence of amino acid residues, by solution and solid phase synthesis. However, unless the peptides can be formed into the correct spatial configuration, i.e. fold correctly, the product will usually be physiologically deficient. A critical step in the folding of proteins is the formation of disulfide bonds from cysteine residues. This is an oxidative step in which sulfhydryl groups are converted to disulfide bonds, thereby forming bridges which assist in folding the peptide or protein into a desired configuration.

Among the conventional methods for the formation of disulfide bonds, air oxidation in aqueous medium is the most commonly used (1–3). Air oxidation usually requires a long duration at basic or neutral pH for completion and a high dilution of peptide or protein concentration to be effective. Nevertheless, it enjoys an advantage that it produces water as a harmless byproduct of the reaction. A variation of the air oxidation method is the thiol-disulfide interchange reaction using a mixture of reduced and oxidized glutathiones (3). The mixed disulfide interchange method is usually effective in the basic pH range. Because the air oxidation and the mixed disulfide interchange method are slow processes, they allow equilibrations of different conformers to produce thermodynamic controlled products. In contrast, strong oxidizing agents such as $I_2$ and $K_3Fe(CN)_6$ that produce kinetic-controlled products are often used for simple peptides containing only a single disulfide bond (4–5). These sulfur-sulfur forming agents are such powerful oxidants that the oxidations are usually performed under carefully controlled conditions to prevent over oxidation. They have the advantage of being applicable in the acidic range, but suffer from the limitation that byproducts generated usually require extensive purification procedures. Several nucleophilic amino acids such as Met, Tyr, Trp, and His are particularly susceptible to these strong oxidants (6). Because of these limitations, strong oxidizing agents are seldom used for the simultaneous refolding and disulfide formation of multi-disulfide bonded peptides or proteins.

Despite these disadvantages, the oxidation methods using air or mixed disulfides are useful for many syntheses, particularly for those involving acidic peptides or proteins (7). However, for basic and hydrophobic peptides that tend to aggregate and precipitate out of solution at or near their basic or neutral isoelectric points during the folding process, the air or mixed disulfide methods for oxidation are not satisfactory. It has been observed that this is the case in the synthesis of several basic and hydrophobic disulfide-rich peptides. In the synthesis of a series of viral growth factors (8–9), the disulfide formation by air oxidation or mixed disulfide method produced precipitation even in the presence of a strong denaturant such as 6M urea. The precipitation resulted in unacceptably low yields of the desired product.

It is, therefore, highly desirable to devise a new method for disulfide formation that is similar in mildness to air oxidation but can be conducted under acidic conditions at an efficient rate with no harmful byproducts.

THE INVENTION

A facile oxidation method has now been discovered which alleviates the disadvantages aforesaid. The preferred oxidizing agent employed in the novel method is dimethyl sulfoxide (DMSO) because it is a common laboratory reagent readily available at reasonable cost. The invention will be described, for convenience, as applied to this preferred oxidant.

Those skilled in the art will recognize that other hydrocarbon sulfides may be similarly employed including substituted hydrocarbons in which hydrogen is replaced with a reaction inert substituent such as hydroxy or halogen. These include symmetrical and non-symmetrical dialkyl sulfoxide containing up to six carbon atoms and further compounds in which the sulfur atom and the carbon atoms to which it is joined form a cyclic alkylene sulfoxide containing 4 or 5 carbon atoms. Typical examples of oxidants containing up to six carbon atoms which are useful in the invention include diethyl and dipropyl sulfoxide, methyl 2-hydroxyethyl sulfoxide, ethyl propyl sulfoxide and tetramethylene sulfoxide.

DMSO has been known as a mild oxidizing for simple organic thiols producing water and dimethyl sulfide (DMS) as harmless byproducts (10–15). It has not, however, heretofore been employed to form disulfide bridges in the oxidative folding of peptides and proteins, nor have the advantages of such use been predicted or realized. Such folding, as will be known to the skilled artisan may involve ring formation on the same molecule or the formation of disulfide bridges on adjacent molecules.

The process of the invention is particularly useful because it is applicable to a wide variety of protein and peptide products at ambient temperature over a wide pH range during a convenient time interval. It is, moreover, applicable to all types of peptide and protein materials including acid, basic, hydrophilic and hydrophobic products, even those containing 500 or more amino acid residues. A particular advantage is that the procedure is applicable to peptides and proteins containing amino acid residues particularly susceptible to oxidative side reactions such as Met, Trp, Tyr, and His.

The invention, accordingly, provides a method for the oxidative folding of a peptide or protein substrate containing reactive sulfhydryl groups to form disulfide rings on bridges by reacting the substrate in an aqueous media with DMSO or equivalent sulfoxide at a pH of form about 2 to about 10.

THE DRAWINGS

FIG. 1 represents model peptides based on basic fibroblast growth factor (FGF) sequence 100–115. The amino acid is denoted by the one-letter code. The nomenclature of the analog (e.g. TY-11(6)) is denoted by the amino acids at each end of its sequence (TY), the number of amino acids in the peptide chain (11) and in the disulfide loop (6, in parenthesis).

FIG. 7 shows $C_{18}$ reverse phase HPLC of synthetic human defensin. (A) Crude defensin after HF cleavage. The reduced defensin eluted at about 19 min. (B) Folding and disulfide formation of crude defensin in 20% DMSO at pH 6(Run 7). The folded defensin eluted at about 14 min, 5 min ahead of the reduced and unfolded defensin. (C) Folding and disulfide formation using air oxidation after 42 hr (Run 1). Similar profile was obtained from Run 2. (D) Purifed defensin of Run 7. The peak with an asterik was cresol which served as an elution standard.

DETAILED DESCRIPTION OF THE INVENTION

The series of basic peptides shown in FIG. 1 derived from the receptor-recognition site comprised of residue 100 to 115 of human basic fibroblast growth factor (15) was used as models to show the effectiveness of DMSO as an oxidizing agent in accordances with the invention. The peptides derived from an antiparallel-strand of FGF and is rich in aromatic as well as - branch amino acids including a Trp, two Thr residues, and three Tyr residues. This highly basic and hydrophobic sequence contained no cysteine but was converted to cysteinyl-containing sequences to establish the utility of the invention. The cationic nature of these peptides was retained as the basic tetrapeptide, Arg107-Ser108-Arg109-Lys110, which was used as the core unit for all models. However, both the length of the peptides from 11 to 16 residues and the size of the disulfide rings from 6 to 11 amino acid residues were varied to determine the generality of the DMSO oxidation method.

The peptides were synthesized according to known procedures using the Boc-benzyl protecting group strategy by the solid-phase method on the p-methyl-benzhydrylamine resin (16). After the low-high HF cleavage (17, 18), the deblocked peptide-carboxamide was dissolved into an aqueous acetic acid solution at a concentration of about 0.5 mg/ml, adjusted to pH 6, with a buffer and diluted to the appropriate volume in DMSO to initiate the disulfide formation.

In each instance, it was observed that the desired oxidative folding took place with the formation of disulfide bonds with the desired ring sizes as shown in FIG. 1.

Figure 2:
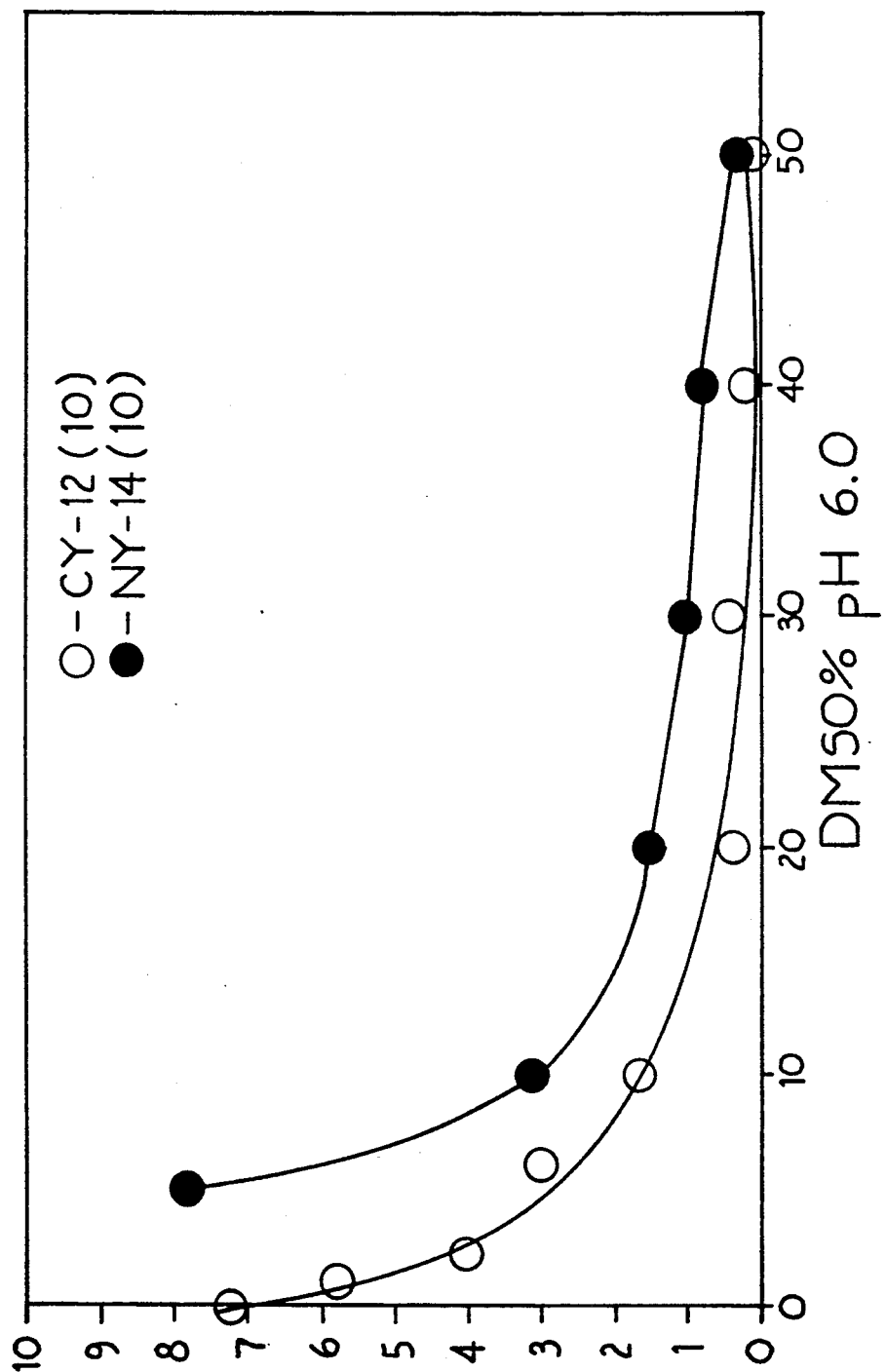
FIG. 2 shows the concentration of DMSO vs time required for completion of disulfide formation. The sequence of the 12-residue peptide CY-12(10) is CTYRSRKYTCWY and the 14-residue peptide NY-14(10) is NYCTYRSRKYTCWY.

Subsequent reactions were conducted to define operative ranges of concentrations of DMSO in aqueous reaction media for the completion of the oxidation reaction. Two model peptides were used to determine the stoichiometric requirements of DMSO. Various concentrations of DMSO ranging from 1 to 50% were added to the aqueous reaction mixtures of two model peptides (FIG. 2). With 12-residue peptide, CY-12(10), disulfide formation was observed to be completed in about 1 hr when the volume ratios of DMSO were from 10 to 30%. The rates increased as the concentration of DMSO increased. At 40 to 50% DMSO, the reaction was completed within 0.5 hr. On the other hand, at concentrations below 5%, the reaction was prolonged to 2 to 6 hr. In the absence of DMSO and under conventional air oxidation conditions, the reaction required more than 7 hr for completion. Similarly, with a 14-residue peptide, NY-14(10), complete reaction was observed in 2-3 hr in 10 to 30% DMSO, and within 1 hr in 40 to 50% DMSO, but more than 10 hr in 1 to 2% DMSO and 24 hr in the absence of DMSO under air oxidation conditions. Since DMSO was intended both as a solvent and as an oxidant, a rather arbitrary midpoint concentration, 20% of DMSO by volume, was used for all subsequent experiments.

Using 20% DMSO in aqueous solution as the oxidative folding reagent, the disulfide formation by the DMSO oxidation was rapid in all model peptides studied. A 50% conversion to the disulfide was found to be effected in about 5 to 30 minutes. The reaction in was followed by analytical $C_{18}$ reverse-phase HPLC (Table 1 and 2). At the completion of the disulfide formation, the solution was diluted two fold and loaded directly to a preparative reverse-phase HPLC for purification to give 32 to 46% overall yield. The integrity of each purified peptide was determined by Cf-252 fission ion mass spectrometry and the observed molecular mass was found to agree with the calculated values. In contrast, parallel experiments using air oxidation at pH 8.0 in the absence of DMSO were found to require 4 to 72 hr for completion. In some cases, air oxidation did not result in the formation of any significant amount of products (Table 2).

The next study was conducted to establish that the reactions of the invention could be conducted without adversely affecting nucleophilic amino acids such as Met, Trp, Tyr, and His. These acids were treated in aqueous buffered solutions at pH 3 to 8 containing 20% DMSO for a 72 hr period. Under these conditions, Met is readily converted to methionine sulfoxide [Met(0)]. However, the sulfide-sulfoxide interchange reaction (19) is known to occur only in strong acidic media due to the weak basicity of DMSO (pka-1.80). No [Met(0)]formation was observed in a solution of 20% DMSO at the pH range between 3 to 8. Similarly, no oxidative reaction was observed with other nucleophilic amino acids such as Trp, Tyr, and His.

The next study was conducted to establish the rates of disulfide formation under the conditions of the invention.

The purified and reduced peptides were used for detailed kinetic studies in 20% DMSO at pH 3 to 8, a range that is practical for laboratory use. For comparison, parallel experiments were performed by air oxidation at various pH values without DMSO. The optimal pH range for disulfide formation in peptides and proteins by DMSO was found to be between 3 to 8, although it is possible to extend this range to as wide as from about 2 to 10 with some peptide or protein substrates. At a pH lower than 3, denaturation may occur. Additionally, there is increasing danger of oxidation of Met to Met sulfoxide at low pHs. The pka of the sulfide in Met is about $-1.8$ and the oxidation of Met to Met sulfoxide by DMSO would be favored by acidic conditions below pH 2. At pH higher than 8, disulfide interchange was found to be quite rapid. For example, the rate constant for the disulfide interchange in a protein at pH 8 is 10 sec $^{-1}M^{-1}$(20).

The rates of disulfide formation of a series of model peptides in DMSO were studied at pH 3 to 8. Purified and reduced model peptides with free sulhydryls were treated in various buffers in 20% DMSO. Since DMSO was used in large excess, the pseudo first order rate $k_1$ of disulfide formation was measured. The reaction products were conveniently monitored by $C_{18}$ reverse-phase HPLC since the reduced and oxidized products were usually separated by more than 1 min apart in their elution profiles. Ten model peptides were studied in detail (FIG. 1). within the range of pH3 to 8, the reaction rates obeyed the first order kinetics and varied about 17 fold, between 0.01 min to 0.17 $min^{-1}$ with half-lives between 4 to 69 min. These rate studies established that oxidation with DMSO in the acidic range in accordance with the invention is useful. The size of the disulfide ring from 6 to 11 amino acid residues did not appear to significantly influence the rates of disulfide in DMSO. However, the position of the cysteine had strong effects and two types of rate profiles were observed that were dependent on the particular location of cysteine in the amino acid sequence.

pH Dependent Rate Constants

Figure 3:
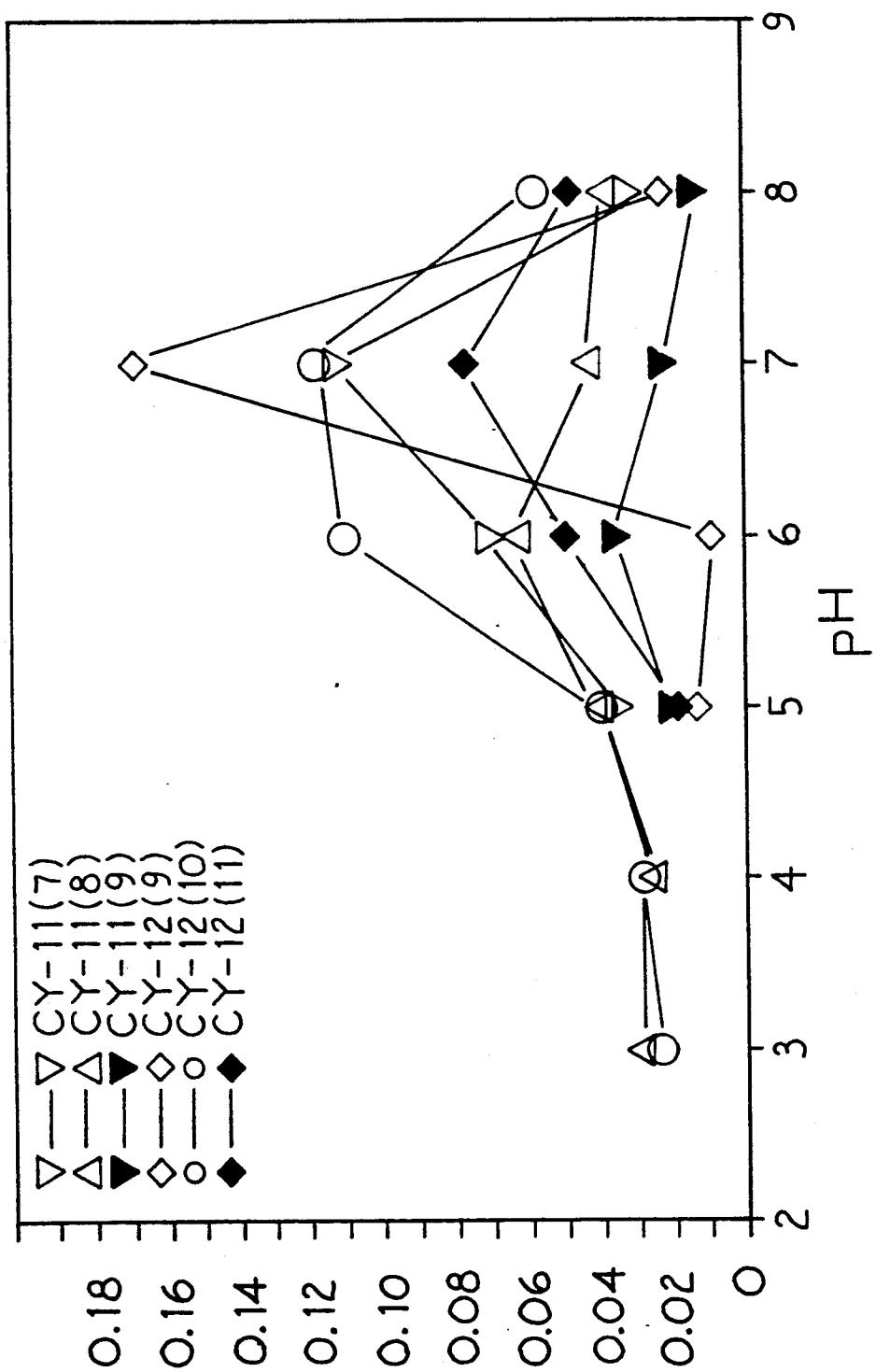
FIG. 3 shows the pH-dependent pseudo first order rates of disulfide bond formation vs. pH in the presence of 20% DMSO.

All six peptides CY-11(7), CY-11(8), CY-11(9), CY-12(9), CY-12(10), and CY-12(11) with a cysteine at the amino terminus showed pH dependence in their rate profiles (Table 1). However, the N-amino group of the amino terminal cysteine must be free. The optimal pH was found to be near neutrality, i.e. from about pH 6 to 7 (FIG. 3). However, the pH dependence could be abolished when the amino terminus was acetylated as in Ac-CY-11(8). (FIG. 3). In contrast, parallel experiments by air oxidation showed that rates were 2 to 12 fold slower at pH 7 and 8, and 10 to 40 fold slower at pH 5 and 6 than DMSO. Below pH 4, rates of disulfide formation by air oxidation were generally too slow to be useful (Table 1 and 2).

· pH-Independent Rate Constants

Figure 4:
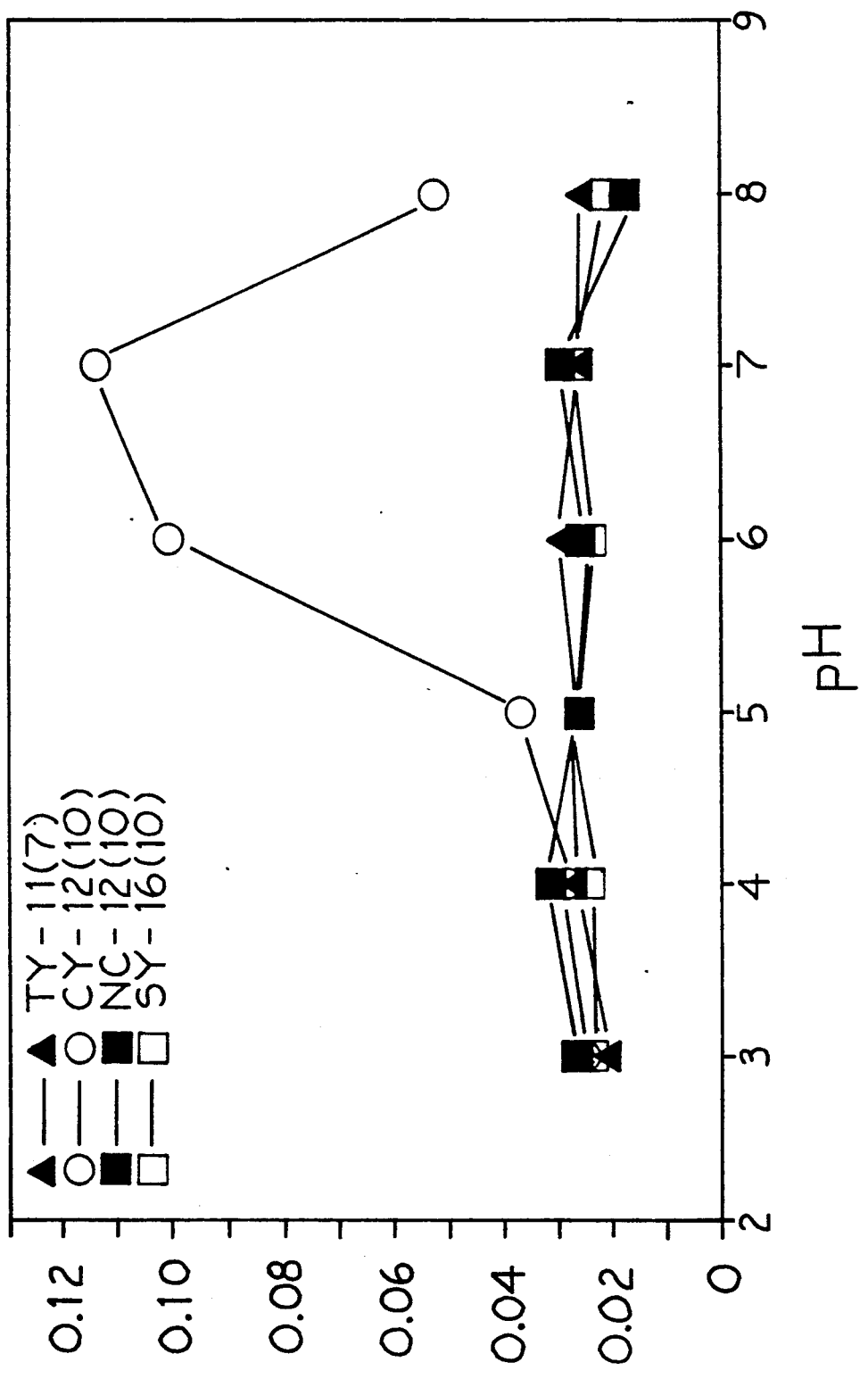
FIG. 4 shows the pH-independent pseudo first order rates of disulfide bond formation vs. pH in the presence of 20% DMSO.
Figure 5:
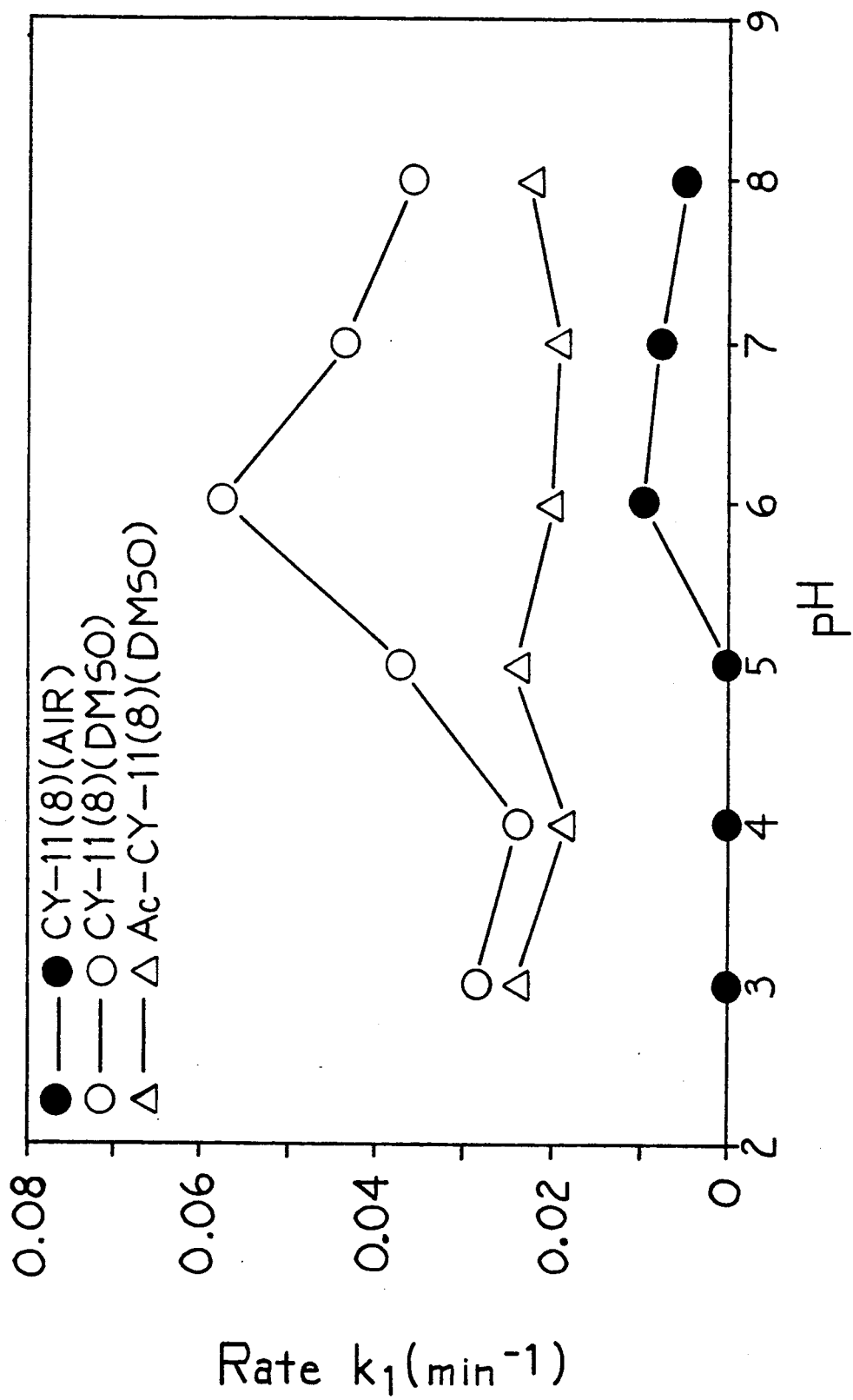
FIG. 5 shows the differences of rate profiles of CY-11(8) in DMSO, after acetylation of the N - amino group, and by air. Note the removal of the free amino group by acetylation of CY-11(8) rendered the rate profiles pH-independent.

All three peptides TY-11(6), NC-12(10), and SY-16(10) with no amino terminal cysteine exhibited pH-independent rate profiles in DMSO oxidation (Table 2). While the peptide CY-12(I0) containing an amino terminal cysteine exhibited pH-dependent rate profile, conversion of the cysteinyl amino group to an amide by acetylation as N-acetylated peptide Ac-CY-11(8), by conjugating a dipeptide as NC-12(10) or a pentapeptide as SY-16(10) led to rate profiles that were pH-independent (FIG. 4). The rates of all four peptides at pH 3 to 8 varied in a very narrow range between 1.8 to 3.2 $min^{-1}$ ($t_{\frac{1}{2}}$ 22 to 39 min) at pH3 to 8. In contrast, very slow rates ($<0.01\ min^{-1}$) were obtained by air oxidation. In two peptides, TY-11(6) and SY-16(10), no products were observed in 72 hr.

Based on the above studies, it was determined that DMSO is an effective, mild oxidizing agent in aqueous buffered media at a pH of from about 2 to 10, preferably about 3 to 8, and most preferably 6 to 7 for the oxidative folding of peptide and protein substrates containing sulfhydryl groups to form disulfide bonds. The reaction can be usefully conducted without adverse effects even with substrates containing amino acid residues readily susceptible to oxidation such as Tyr, His, Met and Trp.

The reaction may be conducted at ambient temperature, i.e. at about 20° C. to 45° C.

Any of a variety of organic and inorganic buffers can be usefully employed in the practice of the invention. The selection of a particular buffer is a mater of convenience and not critical. Tris buffer is preferred because it is readily available and its use normally results in good yields. However, other buffers such as phosphate and acetate buffers can be employed, as can ammonium carbonate, acetate or formate.

The time of the reaction varies over a wide range, typically from about 0.5 to 20 hours. It has been observed that the optimum reaction period varies directly with the length of the molecule to be oxidized. For shorter peptides e.g. those containing about 10 to 20 amino acid residues, reaction periods of less than 2 hr, even as low as 0.5 hr may often be useful. It is rarely necessary to conduct the reaction for more than three hours even with substrate containing 70 or more amino acid residues.

It will be apparent that a molar excess, usually a large molar excess of DMSO is always employed, principally because it is also employed as a solvent. In fact, very little water need be present in the buffered reaction mixture. The preferred concentration of DMSO is from about 20% to 50% by volume, but wide variations are possible, for example from about 5% by volume to 95% by volume, or even higher.

The procedure of the invention can be employed for the preparation of useful compounds such as the defensins.

Figure 6:
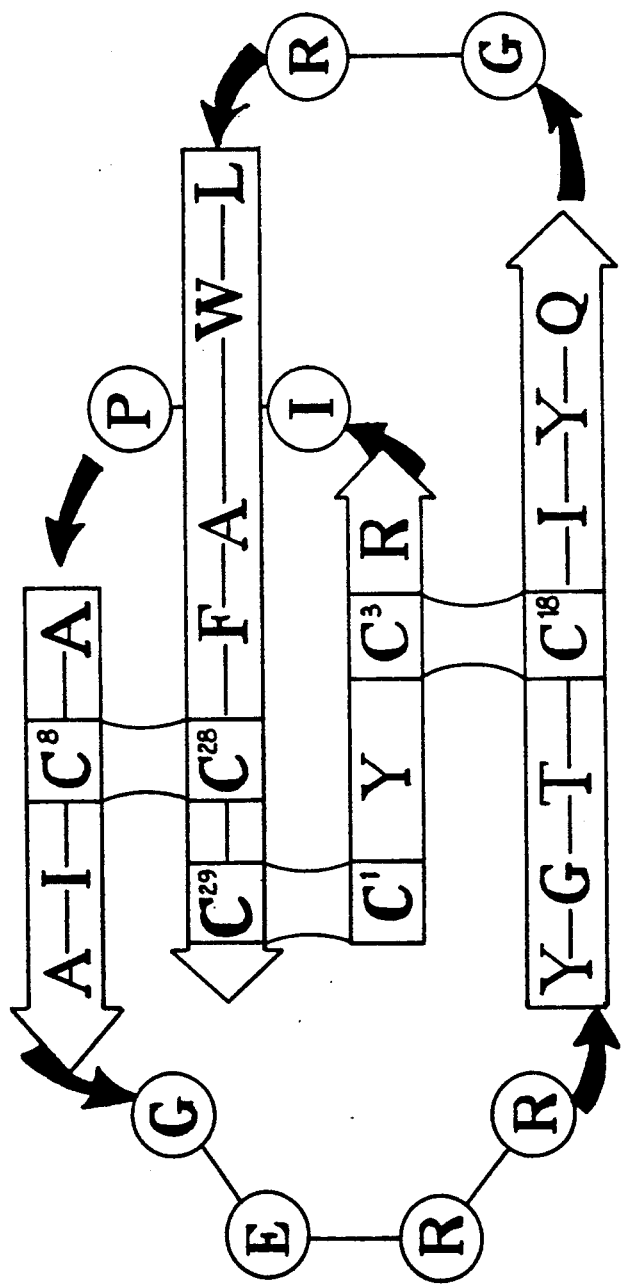
FIG. 6 shows the sequence and disulfide pairings of human defensin.

Defensins are cysteinyl rich, cationic, and antimicriobial peptides produced by mammalian neutrophils as a non-adaptive mechanism in host defenses against bacteria, fungi, and viruses (21). Defensins are stored in cytoplasmic granules and released as one of the cytotoxic effectors by the polymorphonuclear leukocytes when in contact with the pathogens. The primary sequences of 13 different defensins have been determined (22). They all range from 29 to 32 residues with 50 to 80% in sequence relatedness. The structural characteristics of defensins include the invariant 6 Cys and 2 Gly as well as 2 Arg that impart the cationic characteristic of defensins. The three disulfide pairs of defensins constitute a distinctive disulfide motif of this family with of a pairing pattern of 1-6, 2-5, 3-4, starting from the amino-terminus (FIG. 6). The solution structure of defensins have been determined and is found to consist exclusively of-sheets and reverse turns (23).

The challenge for the chemical synthesis of defensins lies in the difficulties of refolding and the formation of the S-S bonds contributed by two factors: (1) the presence of -sheets which tend to aggregate leading to polymeric formation, (2) the strong basic character of defensins that tend to precipitate in the basic condition during disulfide formation. In view of these difficulties, the folding and oxidation in the chemical synthesis of defensins are a stern and suitable test for the S-S formation conditions by the DMSO method of this invention under acidic conditions that would minimize aggregation and precipitation.

The protection scheme for the synthesis of human defensin utilized the conventional protecting group approach of the Boc-benzyl strategy. The deprotection scheme utilized the gradative deprotection approach (24) that removed most of the side chain protecting groups successively while the peptide chain was anchored onto the resin support. The peptide chain, the thiol protecting groups and the tosyl Arg were then removed by the high-HF procedure.

The folding and disulfide formation of the crude synthetic peptide were determined under a series of conditions (Table 30). Seven experiments were performed each employing 100 mg of peptide-resin. In Run 1 to 4, the normal conditions of refolding were used. The crude peptide after the low-high HF treatment was solubilized in 8M urea or 6M guanidine hydrochloride in 0.1 M Tris buffer at pH 8.2 and was dialyzed successively in a lower concentration of the denaturants at pH 8.2 using a Tris buffer in the absence of air to exclude the reducing agent, dithiothreitol. Copious precipitation occurred during all stages of the dialysis. In run 1, the crude peptide contained in both solution and precipitate were folded at the 2M urea stage by air oxidation (FIG. 7). After 18 hr, more precipitation was observed. The soluble portion was subjected to purification by reverse-phase HPLC and yielded 0.4 mg (<1% overall yield) of defensin. Similar procedures in Run 2 using a 1:1 mixture of reduced and oxidized glutathione did not diminish the amount of precipitation during the folding or increase the yield of theproduct. Similar procedures were repeated using guanidine HCl as the denaturant in Run 3 and 4. However, precipitation occurred during the 4M guanidine HCl step. Folding by the mixed disulfide procedure yielded a very small amount of defensin (<1%).

The results of Run 1 to 4 show that defensin favors aggregation at the basic pH that is near the isoelectric point of defensin. Attempts to lower the concentrations of the denaturants lead to aggregation and copious precipitation of the peptide from the solutions. In contrast, three different methods using DMSO as oxidants (Runs 5 to 7) produced significantly higher yields and greatly minimized the precipitation problem. To minimize aggregation, a high dilution method was used in Run 5. In the high dilution method, the peptide in 6M guanidine solution was slowly added to a solution of 1M guanidine at pH 8.2 containing 20% of DMSO during 20 hr with gentle stirring. Under such conditions, the aggregation leading to precipitation was greatly minimized and the sulfur-sulfur bond formation was greatly accelerated. Indeed, the precipitation was minimal and after purification by reverse-phase HPLC, 9.5 mg of defensin (15% overall yield) was obtained.

To avoid the precipitation problem completely, Runs 6 and 7 were conducted at the acidic buffer range (FIG. 7). In Run 6, the crude peptide was dissolved in 8M urea and Run 7 in 6M guanidine HCl, both in Tris buffered solution at pH 6. Dilution of this solution to 1M solution at pH 6 did not result in precipitation and S—S bond formation was conducted at pH 6 in the presence of 20% DMSO. Oxidation was completed in 8 hr to yield 6 (Run 6) and 8.7 mg (Run 7) of defensin after purification from reverse-phase HPLC. The integrity of defensin was determined by Cf-232 fission ion mass spectrometry and found to agree with the expected value. The biological activity of defensin was also found to be as active as the natural defensin.

The process of the invention proved useful in the synthesis of the known vasoconstrictor, endothelin (ET) and its precursor big endothelin (BET). ET a 21-residue bicyclic peptide, and BET, its 38-residue precursor each contain two disulfide bonds.

The pattern of the disulfide pairing (starting from the amino terminus) favors formation of two isomers: the desired isomer with disulfide pairing of 1-4 ($Cys^{1,15}$) and 2-3 ($Cys^{3,11}$) and the major misfolded isomer with disulfide pairing of 1-3 ($Cys^{1,11}$) and 2-4 ($Cys3,15$). Using DMSO oxidation, the 1,4- to 1,3-isomer ratio was found to be 3:1 in both ET and BET. Both synthetic ET and BET were found to contain the expected molecular mass as determined by Cf-252 fission ion mass spectrometry and the expected biological activity.

ET and BET were synthesized on the Pam-resin (25) using the Boc-benzyl strategy by the stepwise solid-phase peptide synthesis. At the completion of the synthesis, Cys(Acm), His(Dnp), Trp(For) and the oxygen-linked protecting groups were sequentially removed while the peptide was still attached to the resin (26). To remove the Cys(Acm) group, the peptide-resin was treated with a 0.06M Hg(OAc)2 in DMF in the dar at 20° for 3 hr (16). The $Hg^{2+}$ salt was removed by washings with DMF and DMF-mercaptoethanol (9:1, v/v). His(Dnp) was then removed with 1M thiophenol in DMF. Finally, the oxygen-linked protecting groups and Trp(For) were removed by the low-TFMSA procedure (17) using a mixture of TFMSA:TFA:DMS (dimethylsulfide): EDT (ethanedithiol): p-cresol (7.6:57.4:25:5:5, v/v) at 4° for 1 hr. After the removal of the aromatic scavengers by repeated washings, the peptide without the protecting groups was cleaved from the resin by a more acidic mixture consisting of TFMSA:TFA:thioanisole:EDT (8:80:8:4, v/v) at 4° for 40min. Each peptide resin was then washed three times with TFA and $CH_2Cl_2$, dried and treated with the high-HF step for 30 min (16). The high HF contained 90% HF, 7.5% p-cresol, and 2.5% p-thiocresol and was conducted in a HF apparatus in a well-ventilated hood. The crude peptide was extracted from the resin and was dialyzed (or through gel permeation) in 4M urea at pH 8.2, 0.1M Tris.HCl and folded by 20% DMSO at pH 6 in a 2M urea solution, pH 8.2, 0.1M Tris.HCl buffer for a period of 8 hours at ambient temperature. Purification of the refolded and oxidized ET by C 8 reverse-phase HPLC gave a homogeneous product. The yields of ET and BET were 1% and 8% respectively.

Table 4 illustrates the use of a variety of sulfoxides under varying conditions in the successful practice of this invention.

Table 5 shows the application of the invention to a number of high molecular weight substrates including those illustrated below under a variety of conditions employing DMSO as the oxidant.

The process of this invention has many advantages over conventional oxidative refolding with air.

DMSO is a mild oxidizing agent for thiols producing $H_2O$ at all concentrations and thus a high concentration of DMSO can be used to bring about desirable rates of reaction. Since DMSO can be used as both a solvent and an oxidant at a very high concentration, the disulfide formation by DMSO is rapid and most disulfide formation is observed to be completed within a few hours. Furthermore, a wide range of pH can be used in the DMSO method. With air oxidation, the condition is usually limited to basic conditions above pH 7. Thus, the wide operable pH range including the acidic pH provides a wide range of options for the oxidation of basic or neutral peptides and proteins which are often found to be insoluble or precipitated under the neutral or basic conditions. Similar advantages apply to the other sulfoxides which can be utilized in the practice of the invention.

TABLE 1

Comparison of pH-Dependent rates of disulfide formation by DMSO and air oxidation $10^2 k_1 (min^{-1})^a$

| pH | CY-11 (7) | CY-11 (8) | CY-11 (9) | CY-12 (9) | CY-12 (10) | CY-12 (11) |
|----|-----------|-----------|-----------|-----------|------------|------------|
| 8 | 3.1 (1.3)[c] | 3.8 (0.5) | 1.4 (0.2) | 2.4 (0.3) | 5.4 (1.0) | 4.4 (2.0) |
| 7 | 11.2 (1.6) | 4.6 (0.8) | 2.4 (0.2) | 17.0 (4.5) | 11.8 (1.4) | 8.1 (1.2) |
| 6 | 6.6 (0.7) | 6.1 (1.0) | 3.7 (0.2) | 1.0 (0.2) | 10.3 (0.8) | 5.0 (0.8) |
| 5 | 3.5 (0.3) | 4.0 (<0.01) | 1.9 (0.1) | 1.3 (0.2) | 3.9 (<0.01) | 1.9 (0.1) |
| 4 | — | 2.6 (<0.01) | — | — | 2.8 (<0.01) | — |
| 3 | — | 3.1 (<0.01) | — | — | 2.6 (<0.01) | — |

[a]pseudo first order rates;
[b]see FIG. 1 for compound designation;
[c]the rates of air oxidation are in parentheses.

The advantages of the invention are readily apparent.

TABLE 2

Rates of disulfide formation by DMSO (pH-independent) and air oxidation $10^2 k_1 (min^{-1})^a$

| pH | TY-11 (6) | NC-12 (10) | SY-16 (10) | Ac-CY-11 (8)[b,c] |
|----|-----------|------------|------------|-------------------|
| 8 | 2.7 (<0.01)[d] | 1.8 (0.02) | 2.2 (<0.01) | 2.3 (<0.01) |
| 7 | 2.6 (<0.01) | 2.9 (0.002) | 2.7 (<0.01) | 2.0 (<0.01) |
| 6 | 3.2 (<0.01) | 2.7 (0.005) | 2.5 (<0.01) | 2.1 (<0.01) |
| 5 | 2.7 (<0.01) | 2.7 (0.004) | 2.7 (<0.01) | 2.5 (0.02) |
| 4 | 2.7 (<0.01) | 3.2 (0.001) | 2.4 (<0.01) | 2.0 (0.01) |
| 3 | 2.2 (<0.01) | 2.8 (0.003) | 2.5 (<0.01) | 2.6 (0.02) |

[a]pseudo first order rates;
[b]see FIG. 1 for compound designations;
[c]N-acetylated compound of CY-11 (8);
[d]the rates of air oxidation are in parentheses.

TABLE 3

Comparison of different methods of disulfide formation in defensin

| Run | Condition[a] | pH | Oxidant | Yield (%) | Precipitation |
|-----|--------------|----|---------|-----------|---------------|
| 1. | urea | 8.2 | air | <1.0 | ++++ |
| 2. | guanidine HCl | 8.2 | air | <1.0 | ++++ |
| 3. | urea | 8.2 | mix. disulfide | <1.0 | ++++ |
| 4. | guanidine HCl | 8.2 | mix. disulfide | <1.0 | ++++ |
| 5. | guanidine HCl-high dilution[b] | 8.2 | DMSO | 14 | + |
| 6. | urea | 6 | DMSO | 10 | — |
| 7. | guanidine HCl-high dilution | 6 | DMSO | 14 | — |

[a]in 2M solution in 0.5 mg/ml of concentration;
[b]slow addition of a 6M solution to a solution of 1M solution containing 20% DMSO;
[c]++++ copious amount of precipitation, nearly 80% or more of the products precipitated from the solution, + slight amount of precipitation, less than 10% of the products precipitated from the solution, — no precipitation observed.

TABLE 4

Low Molecular Weight Sulfoxides for Oxidative Refolding of Disulfides Using CY-12 (10)[1] As A Substrate

| | | Conditions | | |
|---|---|---|---|---|
| Reagent | pH | volume (%) | Time (hr) | Yield (%) |
| Tetramethylene sulfoxide | 8 | 20 | 1 | 99 |
| | 7 | 20 | 1 | 95 |
| | 6 | 20 | 1 | 95 |
| | 5 | 20 | 1 | 94 |
| Ethyl 2-hydroxyethyl sulfoxide | 8 | 10 | 1 | 97 |
| | 7 | 10 | 1 | 95 |
| | 6 | 10 | 1 | 95 |
| | 5 | 10 | 1 | 90 |
| ethyl methyl sulfoxide | 8 | 20 | 1 | 99 |
| | 7 | 20 | 1 | 98 |
| | 6 | 20 | 1 | 98 |
| | 5 | 20 | 1 | 94 |

[1]CY-12 (10) is CTYRSRKTTCWY

TABLE 5

Examples of Oxidative Refolding of Bioactive Peptides and Proteins in DMSO

| Example | Number of amino acids | Number of disulfides | Volume (%) | pH | Time (hr) |
|---------|----------------------|---------------------|------------|----|-----------|
| Human endothelin-1 | 21 | 2 | 20 | 8 | 2 |
| | | | 20 | 6 | 3 |
| Big endothelin-1 | 39 | 2 | 20 | 8 | 2 |
| | | | | 6 | 4 |
| Human transforming growth factor | 50 | 3 | 15 | 8 | 2 |
| | | | 20 | 8 | 2 |
| | | | 20 | 6 | 6 |
| Vaccinia virus | 77 | 3 | 15 | 8 | 4 |
| | | | 20 | 6 | 6 |
| | | | 10 | 6 | 6 |
| | | | 15 | 6 | 6 |
| | | | 20 | 6 | 5 |
| Heparin-binding epidermal growth factor (1-79) | 79 | 3 | 15 | 8 | 8 |
| | | | 20 | 8 | 7 |
| | | | 20 | 6 | 12 |
| | | | 20 | 7 | 12 |
| Insulin growth factor-1 | 70 | 3 | 10 | 8 | 6 |
| | | | 10 | 6 | 18 |
| rubonuclease | 124 | 4 | 20 | 8 | 10 |
| | | | 20 | 6 | 10 |

The following section of this specification illustrates the process of the invention including the preparation of peptide substrates the oxidative folding as well as the studies conducted to illustrate the efficacy and utility of the DMSO oxidative procedure.

Solid-Phase Peptide Synthesis of Peptides

The monocyclic peptides were synthesized by the solid-phase method (2,11) using 4-methylbenzhydrylamine resin at a substitution level of 1.1 mmol/g while the defensin were prepared using 4-(Boc-aminoacyloxymethyl)-phenylacetamidomethyl-resin at 0.8 mmol/g substituion level (27). Typically, 0.3 to 0.6 g of resin was used for each synthesis. All amino acids were protected with N-tertbutyloxycarbonyl (Boc). Side chain protecting groups were: Arg(Tos), Asp(OcHex), Cys(Acm), Cys(4-MeBzl), Glu(OBzl), His(DnP), Lys(2-ClZ), Ser(Bzl), Thr(Bzl), Tyr(BrZ), and Trp(For). Each synthetic cycle consisted of (i) a 20-min deprotection with 50% trifluroacetic acid/$CH_2Cl_2$, (ii) neutralization with 5% diisopropylethylamine/$CH_2Cl_2$, and (iii) double coupling with preformed symmetrical anhydrides (6 equivalents of the Boc-amino acid) for 1 h each in $CH_2Cl_2$ and then in dimethylformamide (DMF). Couplings of Boc-Asn-OH, Boc-Gln-OH, and Boc-Arg-(Tos) were mediated by the preformed hydroxybenzotriazole active ester in DMF. Boc-Gly-OH was coupled with dicyclohexylcarbodiimide alone. All couplings were monitored by the quantitative ninhydrin test (28).

HF Cleavage

Protected peptide-resin (0.2 to 0.4 g) was first treated 3-5 times with 1M thiophenol in DMF for 8-12 h to remove the $N^{im}$-dinitrophenyl protecting group of His(29) and then with 50% trifluoroacetic acid/$CH_2Cl_2$ (10 ml) for 5 min to remove the N-tertbutyloxycarbonyl group. The dried peptide-resin was treated with the low-high HF method of cleavage. For the low HF treatment, the peptide-resin was premixed with dimethylsulfide, p-thiocresol, and p-cresol. Liquid HF at $-78°$ C. was then added to give a final volume of 10 ml (65:2.5:7.5:25,v/v). The mixture was equilibrated to $0°$ C. by stirring it in an ice bath. After 2h, the HF and dimethylsulfide were removed in vacuo. The high HF treatment was initiated by recharging the reaction vessel at $-78°$ C. with 14 ml of fresh liquid HF to give a total volume of 15 ml of HF-p-cresol-pthiocresol. The reaction was carried out at $0°$ C. for 1 h. HF was removed by evaporation at $0°$ C. After washing with cold ethermercaptoethanol (98:2, v/v, 30 ml) to remove p-thiocresol and p-cresol, the crude reaction mixture was extracted with different buffers at the completion of the synthesis.

Purification and Oxidative Folding of Disulfide Peptides

All peptide analogs were purified by $C_{18}$ reverse phse HPLC using a gradient of 5% $CH_3CN$ containing 0.0445% $CF_3CO_2H$, and 60% $CH_3CN$ containing 0.039% CF Air oxidation in pH 8.0 buffer (0.1M ammonium bicarbonate/carbonate) was used for the oxidation of the monocyclic analogs. For the tricyclic defensin, the 8M urea solution containing the crude mixture of peptide was sequentially dialyzed (Spectra Por 6, MW cutoff 1000) at $0°$ C. for 8-16 h against 4 I each of deaeriated and $N_2$-purged 8, 6, 4, and 2 M urea, all in 0.1M Tris buffer, pH 8.2. In case of guànidine HCl, the dialysis was against 4 I each of deaeriated 6, 3, and 1M guanidine HCl in 0.10M Tris buffer, pH 8.2. Since the basic character of defensin favored aggregration leading to precipitation at the low concentrations of denaturant, a high dilution method was performed. The peptide solution at high concentrations of an denaturant (70 ml of 6M guanidine HCl) was added slowly by peristaltic pump into a 0.1M Tris. HCl solution (330 ml) containing 24.24% DMSO at pH 8.2. Oxidation and disulfide formation of defensin by the mixed disulfide method was performed in 2M urea, pH 8.0 Tris HCl buffer (200ml), in 1.5 nM oxidized and 0.75 nM reduced glutathione for 16-48 h. The clear solution was dialyzed against 8I each of 0.1M Tris, pH 8.0 and 1 MHOAc. The peptides were purified by C-18 reverse-phase liquid chromatrography (2.5×30 cm) eluted with 0.05% TFA-$CH_3CN$. Amino acid analysis was carried out in 5.7 N HCl at $110°$ C. for 24 h and the experimental results agreed well with the values. Cf-252 fission mass spectrometry was used to measure all monocyclic peptides. The observed values agreed with the calculated values wiht a deviation less than 0.5 mass unit. The $(M+4H)^{4+}$ of defensin was found to 843.55 and $(M+3H)^{3+}$ was found to be 1124.4. Both gave a measured molecular weight of 3370.2 which agreed well with the calculated value of 3370.8.

Oxidation by DMSO

After the HF cleavage, the peptides derived from 200 to 400 mg of peptide resin with an initial substitution at 1.1 mmol/g was first extracted three times by a mixture of ether-mercaptoethanol (98:2, v/v) to remove the organic scavengers. The basic peptide was extracted first with 25 ml of 25% acetic acid (higher concentration when the peptide was not soluble) and a second extration with 50 ml of 5% acetic acid. The combined acetic acid was diluted to 250 ml to a final concentration of 5% acetic acid and its pH was adjusted to pH 6 by $(NH_4)_2CO_3$. To this solution containing the deprotected peptide at a concentration in the range of 0.5 to 1 mg/ml, 20% by volume of DMSO was added. The progress of the oxidation reaction was monitored by analytical $C_{18-}$ reverse phase HPLC. At the completion of the reaction, usually 1-4 hr, the solution was diluted 2 fold by the initial buffer (buffer A of HPLC) and loaded directly into a preparative $C_{18}$-reverse phase HPLC column (Vydac, 10×25 cm, 5 particle size). The desired peptide was then eluted with a linear gradient from 0 to 40-50% buffer B in 45 min. Buffer A contained 5% $CH_3CN$ and 0.0445% $CF_3CO_2H$ and buffer B contained 60% $CH_3CN$ and 0.039% $CF_3CO_2H$.

Oxidation by Air

The solution containing the deprotected peptide at a concentration of 0.2 mg/ml after HF was adjusted to pH 8 by Tris.HCl to a 0.1M concentration. The reaction was slowly stirred and the progress of the oxidation reaction was monitored by analytical $C_{18}$-reverse phase HPLC. The workup was similar to those sample prepared by oxidation by DMSO.

Kinetic Study

The disulfide in each of the ten purified synthetic peptides (FIG. 1) at a concentration of 85 nmol in 25 ul was reduced at pH 8 with dithiothreitol (0.2 umol/5 ul) under nitrogen for 5 min. The reduced peptide was added to a buffered solution (0.5 ml) between pH 3 to 8 containing 20% DMSO. Aliquots (20 ul each) were then withdrawn at various points in time between 2.5 to 5 min interval and quenched by $CF_3CO_2H$ (5 ul in 9% solution) to stop the reaction. The progress of the oxidation was analyzed immediately by $C_{18}$-reversed phase HPLC. The pseudo first order constants (k) were calculated by $kt=In(X_o/X_t)$, where $X_o$ is the initial concentration of the reactant and $X_t$ is the concentration of the reactant remaining at t min. Parallel experiments were performed using air oxidation to obtain the rate constants.

References 1. (a) Li, C.H.; Yamashiro, D.; Gospodarowicz, D.; Kaplan, S.; Van Vliet, G. 1983. Proc. Natl. Acad. Sci. U.S.A. 80, 2216-2220. (b) Yajima, H.; Fujii, N. J. Am. Chem. Soc. 1981 103, 5867-5871.

2 (a) Tam, J. P. 1987. Int. J. Peptide Protein Res. 1987, 29, 421-431. (b) Tam, J. P.; Sheikh, M. A.; Salomon, D. S.; Ossowski, L. Proc. Natl. Acad. Sci. USA 1986, 83, 8082-8086.

3. Ahmed, A.K.; Schaffer, S.W; Wetlaufer, D.B. J. Biol. Chem. 1975 250, 8477-8482.

4. (a) Kamber, B.; Hartmann, A.; Eisler, K.; Riniker, B.; Rink, H.; Sieber, P.; Rittel, W.; Helv. Chim. Acta. 1980 63, 899 915. (b) Veber, S.; Milkowsi, J.D.; Varga, S.L.; Denkewalter, R. G.; Hirschmann, R. J. Am. Chem. Soc. 1972, 94, 5456–5461.

5. Hope, D.B.; Murti, V.V.S.; DuVigneaud, V.J. Biol. Chem. 1962, 237, 1563–1566.

6. Sieber, P.; Kamber, B.; Riniker, B.; Rittel, W. 1980. Helv. Chim. Acta 63, 2358–2363.

7. Tam, J.P.; Marquardt. H.; Rosberger, D. F.; Wong, T. W. and Todaro, G.J. 1984. Nature 309 376–378.

8. (a) Lin, Y. Z.; Caproaso, G.; Chang, P. Y.; Ke, X. H.; Tam, J. P. 1988. Biochem. 27, 5640–5645. (b) Lin, Y. Z.; Ke, X. H.; tam, J. P. 1990. J. Biol. Chem. 265, 18884–19990.

9. Lin, Y. Z.; Tam, J. P. 1990. Biochemistry In press.

10. (a) Wallace, T. J. J. Am. Chem. soc. 1964, 86, 2018–2021. (b) Wallace, T. J.; Mahon, J. J. J.Am. Chem. Soc. 1964, 86, 4099–4103.

11. Goethals, E.J.; Sillis, C. Makromol. Chemie 1968 119, 249–251.

12. Snow, J. T., Finley, J. W. and Friedman M. (1975) Biochem. Biophy. Res. Commun. 64, 441–447.

13. (a) Lowe, O. G. J. Org. Chem. 1975 40, 2096–2098. (b) Lowe, O. G. J. Org. Chem. 1976 41, 2061–2064.

14. (a) Aida, T.; Akasaka, T.; Furukawa, N; Oae, S. Bull. Chem. Soc. Jap. 1976 49, 1141–1142. (b) Kim, J. K.; Lingman, E.: Caserio, M.c. J. Org. Chem. 1978 43, 4545–4546.

15. Abraham, J.A; Whang, J. L.; Tumolo, A; Mergia. A.; Friedman, J. Gospodarowicz D.; Fiddes, J. C. EMBO J. 1986 5, 2523–2538.

16. (a) Merrifield, R. B. J. Am. Chem. Soc. 1963, 85, 2149–2154. (b) Merrifield, R. B. Science 1986, 232, 341–347.

17. (a) Tam, J. P.; Heath, W. F.; Merrifield, R. B. Am. Chem. Soc. 1983, 105, 6442–6455. (b) Tam, J. P.; Heath, W. F.; Merrifield, R. B. 1986. J. Am. Chem. Soc. 1986, 108; 5242–5251.

18. For review on HF cleavage, see (a) Tam, J. P. 1988. In Macromolecular sequencing and synthesis: Selected methods and applications. D. H. Schlessinger, editor. Alan R. Liss, New York 153–184. (b) Sakakibara, S. 1971. In Chemistry and Biochemistry of Amino Acids, Peptides, and Proteins. B. Weinstein, editor. Dekker, New York. 51–85.

19. Perdocin, G.; Soorrano, G. J. Am. Chem. Soc. 1977 99, 6983–6986.

20. Creighton, T. E. 1990. In Protein Folding L. M. Gierasch and J. King, editors. Am. Assoc. Adv. Sci., Washington, D.C. 157–170.

21. Lehrer, R. I.; Ganz, T.; Szklarek, D.; Selsted, M. E. J. Clin. Invest. 1988 81, 1829–1835.

22. Selsted, M. E.; Harwig, S. S. L. J. Biol. Chem. 1989 264, 4003–4007.

23. Pardi, A.; Hare, D. R.; Selsted, M. E.; Morrison, R. D.; Bassolino, D. A.; Bach, A. C. J. Mol. Biol. 1988 201, 625–636.

24 Tam, J. P. 1985. J. Org Chem. 50:5291–5298.

25. Tam, J. P. W. Liu. in Proceedings of the 11th American Peptide Symposium.

26. Mitchell, A. R., Erickson, B. W., Ryabtsev, M. N., Hodges, R. S., Merrifield, R. B. (1976) J. Am. Chem. Soc. 98: 7357–7362.

All references are incorporated by reference herein in their entirety.

What is claimed is:

1. A method for the oxidative folding of peptide and protein substrates containing oxidizable sulfhydryl groups which comprises reacting the substrate in a buffered aqueous medium at a pH of from about 2 to 10 for a period of from 0.5 to 20 hours with a molar excess of a substituted or unsubstituted hydrocarbon sulfoxide selected from the group consisting of symmetrical and non-symmetrical dialkyl sulfoxides containing up to six carbon atoms and further sulfoxides in which the sulfur atom and the carbon atoms to which they are joined are united to form a cyclic aliphatic ring containing four or five carbon atoms.

2. A method for the oxidative folding of peptide and protein substrates containing oxidizable sulfhydryl groups which comprises reacting the substrate in a buffered aqueous medium at a pH of from about 2 to 10 for a period of from 0.5 to 20 hours with a molar excess of dimethyl sulfoxide.

3. A method as in claim 2 wherein the substrate contains at least one amino acid residue selected from the group consisting of methionine, tryptophane, tyrosine and histidine.

4. A method as in claim 2 or 3 wherein the concentration of dimetnyl sulfoxide is from about 5% to 80% by volume.

5. A method as in claim 4 wherein the aqueous medium is buffered with a Tris buffer.

6. A method as in claim 2 wherein the substrate contains about 10 to 20 amino acid residues the reaction period is from about 0.5 to 2 hours.

7. A method as in claim 2 wherein the substrate contains from more than 20 to about 40 amino acid residues and the reaction period is from about 0.5 to 5 hours.

* * * * *